(12) United States Patent
Lubitz

(10) Patent No.: US 6,610,517 B1
(45) Date of Patent: Aug. 26, 2003

(54) COMPARTMENTALIZATION OF RECOMBINANT POLYPEPTIDES IN HOST CELLS

(76) Inventor: Werner Lubitz, Schönborngasse 12/7, 1080 Vienna (AT)

( * ) Notice: Subject to any disclaimer, the term of this patent is extended or adjusted under 35 U.S.C. 154(b) by 0 days.

(21) Appl. No.: 09/889,572
(22) PCT Filed: Jan. 28, 2000
(86) PCT No.: PCT/EP00/00686

§ 371 (c)(1),
(2), (4) Date: Jul. 30, 2001

(87) PCT Pub. No.: WO00/44878

PCT Pub. Date: Aug. 3, 2000

(30) Foreign Application Priority Data

Jan. 28, 1999 (DE) .......................... 199 03 345

(51) Int. Cl.[7] .......................... C12P 21/04; C12P 21/06; C12Q 1/70
(52) U.S. Cl. .......................... 435/70.1; 435/5; 435/7.2; 435/69.1; 424/184.1; 424/234.1
(58) Field of Search .......................... 435/5, 7.2, 69.1, 435/70.1; 424/184.1, 234.1

(56) References Cited

FOREIGN PATENT DOCUMENTS

| DE | 44 17 169 | 11/1995 |
|---|---|---|
| WO | WO 93 10246 | 5/1993 |
| WO | WO 97 28263 | 8/1997 |

OTHER PUBLICATIONS

Valls M. et al.: "Bioaccumulation of heavy metals with protein fusions of metallothionein to bacterial OMPs." vol. 80, No., 10, Oct. 1998 pp. 855–861.
Sleytr U. B. et al.: "Bcterial and Archaeal S–Layer Proteins: Structure–Function Relationships and their Biotechnological Applications" Trends in Biotechnology, vol. 15, No. 1. (156), Jan. 1, 1997, pp. 20–26.
Szostak M. P. et al.: "Bacterial ghosts as multifunctional vaccine particles." Behring Institute Mitteilungen, No. 98, 1997, pp. 191–196.
Lubitz W. et al.: "Extended recombinant bacterial ghost system" Journal of Biotechnology, Bd. 73 Nr. 2–3, Aug. 20, 1999, Seiten 261–273.
International Preliminary Examination Report, PCT/EP00/00686, May 2, 2001.

*Primary Examiner*—Hankyel T. Park
(74) *Attorney, Agent, or Firm*—Rothwell, Figg, Ernst & Manbeck, P.C.

(57) ABSTRACT

The present invention relates to host cells which contain at least two functional recombinant polypeptides, at least one of which is bound to a support, preferably in each case in different cell compartments, for example cytosol, cytoplasmic membrane, periplasm and outer membrane, and also to methods for preparing said host cells. The cells of the invention are particularly, suited as bioreactors for carrying out enzymatic reaction cascades for which compartmentalization of individual enzymes is advantageous or necessary.

16 Claims, 2 Drawing Sheets

Figure 2:
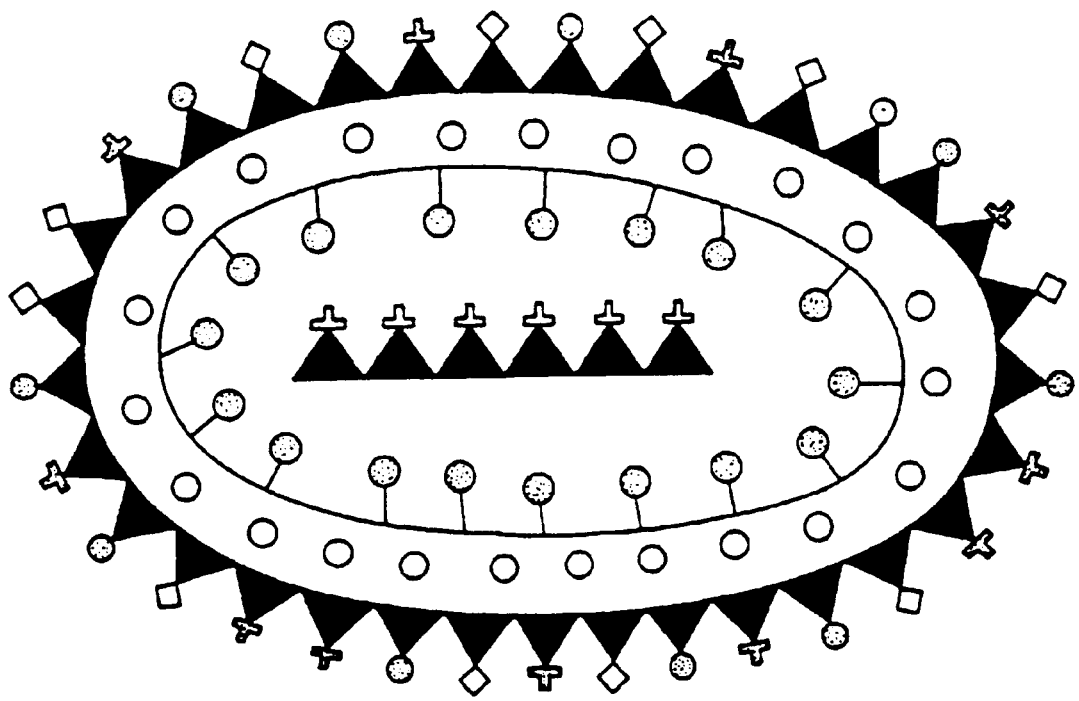
Figure 2:
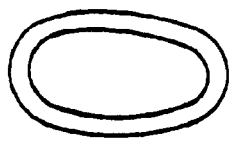
Figure 2:

○ Bacterium
o Enzymes exported into the periplasmic space (pe)
φ Membrane-anchored enzymes (mae)
⊥ S-layer-immobilized enzymes (sie)
⊥⊥⊥ S-layer-immobilized enzymes (sie)

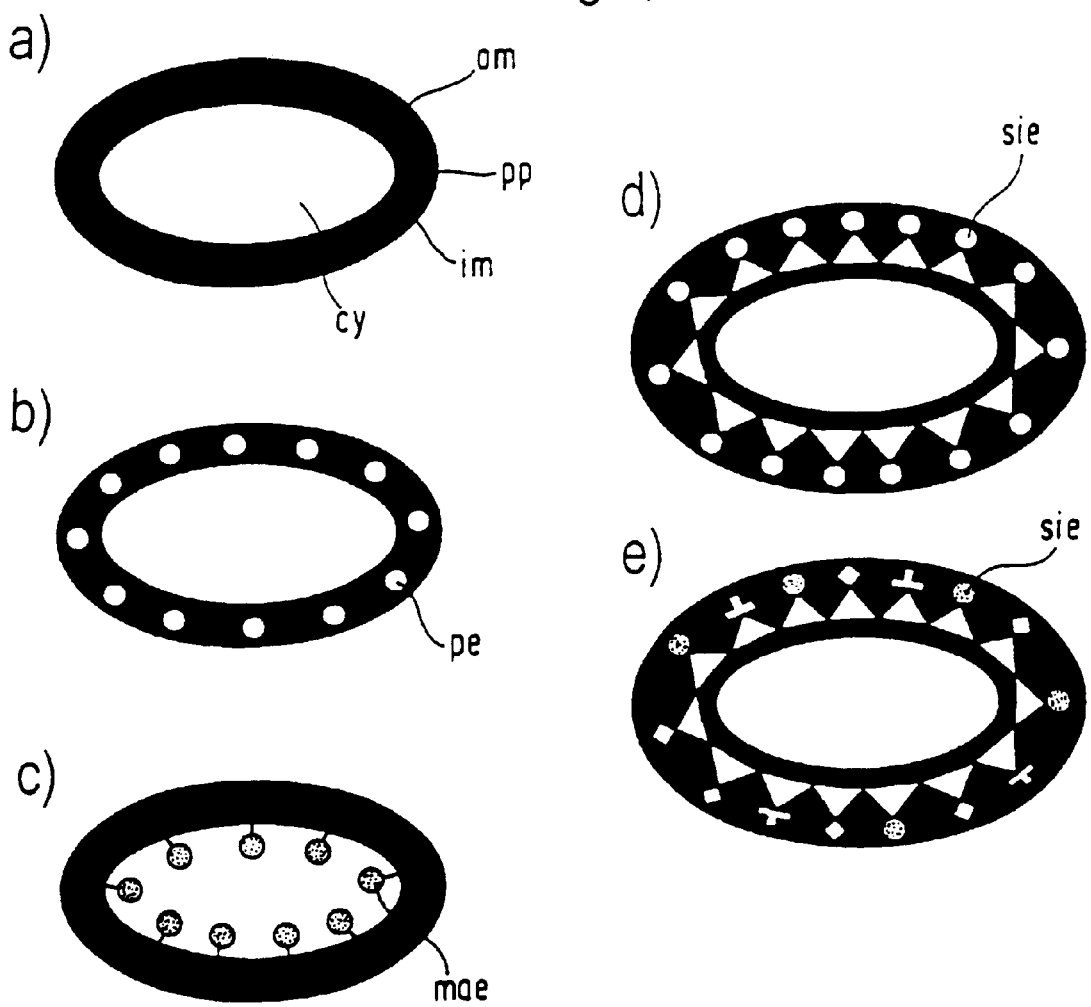
Fig. 1
○ Bacterium
○ Enzymes exported into the periplasmic space (pe)
 Membrane-anchored enzymes (mae)
 S-layer-immobilized enzymes (sie)
 S-layer-immobilized enzymes (sie)

Recombinant bacteria with recombinant S-layers

○ Bacterium

○ Enzymes exported into the periplasmic space

Membrane-anchored enzymes

Recombinant S-layer-based enzyme

SEQUENCE LISTING

<160> NUMBER OF SEQ ID NOS: 4

<210> SEQ ID NO 1
<211> LENGTH: 3687
<212> TYPE: DNA
<213> ORGANISM: Bacillus stearothermophilus
<220> FEATURE:
<221> NAME/KEY: CDS
<222> LOCATION: (1)..(3684)
<223> OTHER INFORMATION:
<221> NAME/KEY: sig_peptide
<222> LOCATION: (1)..(90)
<223> OTHER INFORMATION:
<221> NAME/KEY: mat_peptide
<222> LOCATION: (91)..(3684)
<223> OTHER INFORMATION:

<400> SEQUENCE: 1

```
atg gat agg aaa aaa gct gtg aaa cta gca aca gca agt gct att gca       48
Met Asp Arg Lys Lys Ala Val Lys Leu Ala Thr Ala Ser Ala Ile Ala
-30             -25                 -20                 -15 gca agt gca ttt gtc gct gca aat cca aac gct tct gaa gcg gct aca       96
Ala Ser Ala Phe Val Ala Ala Asn Pro Asn Ala Ser Glu Ala Ala Thr
            -10                  -5                  -1   1 gat gta gca aca gta gta agc caa gca aaa gca cag ttc aaa aaa gca      144
Asp Val Ala Thr Val Val Ser Gln Ala Lys Ala Gln Phe Lys Lys Ala
                5                  10                  15 tac tat act tac agc cat aca gta acg gaa act ggt gaa ttc cca aac      192
Tyr Tyr Thr Tyr Ser His Thr Val Thr Glu Thr Gly Glu Phe Pro Asn
        20                  25                  30 att aac gat gta tat gct gaa tac aac aaa gcg aaa aaa cga tac cgt      240
Ile Asn Asp Val Tyr Ala Glu Tyr Asn Lys Ala Lys Lys Arg Tyr Arg
35                  40                  45                  50 gat gcg gta gca tta gtg aat aaa gca ggt ggc gcg aaa aaa gac gct      288
Asp Ala Val Ala Leu Val Asn Lys Ala Gly Gly Ala Lys Lys Asp Ala
                55                  60                  65 tac tta gct gat tta caa aaa gaa tat gaa act tac gtt ttc aaa gca      336
Tyr Leu Ala Asp Leu Gln Lys Glu Tyr Glu Thr Tyr Val Phe Lys Ala
        70                  75                  80
```

-continued

```
aac cct aaa tct ggc gaa gct cgt gta gca act tac atc gat gct tac   384
Asn Pro Lys Ser Gly Glu Ala Arg Val Ala Thr Tyr Ile Asp Ala Tyr
         85                  90                  95 aac tat gca aca aaa tta gac gaa atg cgc caa gag cta gag gct gct   432
Asn Tyr Ala Thr Lys Leu Asp Glu Met Arg Gln Glu Leu Glu Ala Ala
        100                 105                 110 gtt caa gca aaa gat tta gaa aaa gca gaa caa tac tat cac aaa att   480
Val Gln Ala Lys Asp Leu Glu Lys Ala Glu Gln Tyr Tyr His Lys Ile
115                 120                 125                 130 cct tat gaa att aaa act cgc aca gtc att tta gat cgc gta tat ggt   528
Pro Tyr Glu Ile Lys Thr Arg Thr Val Ile Leu Asp Arg Val Tyr Gly
                135                 140                 145 aaa aca act cgt gat tta ctt cgc tct aca ttt aaa gca aaa gca caa   576
Lys Thr Thr Arg Asp Leu Leu Arg Ser Thr Phe Lys Ala Lys Ala Gln
        150                 155                 160 gaa ctt cgc gac agc tta att tat gat att acc gtt gca atg aaa gcg   624
Glu Leu Arg Asp Ser Leu Ile Tyr Asp Ile Thr Val Ala Met Lys Ala
        165                 170                 175 cgc gaa gta caa gac gct gtg aaa gca ggc aat tta gac aaa gct aaa   672
Arg Glu Val Gln Asp Ala Val Lys Ala Gly Asn Leu Asp Lys Ala Lys
180                 185                 190 gct gct gtt gat caa atc aat caa tac tta cca aaa gta aca gat gct   720
Ala Ala Val Asp Gln Ile Asn Gln Tyr Leu Pro Lys Val Thr Asp Ala
195                 200                 205                 210 ttc aaa act gaa cta aca gaa gta gcg aaa aaa gca tta gat gca gat   768
Phe Lys Thr Glu Leu Thr Glu Val Ala Lys Lys Ala Leu Asp Ala Asp
                215                 220                 225 gaa gct gcg ctt act cca aaa gtt gaa agt gta agt gcg att aac act   816
Glu Ala Ala Leu Thr Pro Lys Val Glu Ser Val Ser Ala Ile Asn Thr
                230                 235                 240 caa aac aaa gct gtt gaa tta aca gca gta cca gtg aac gga aca cta   864
Gln Asn Lys Ala Val Glu Leu Thr Ala Val Pro Val Asn Gly Thr Leu
        245                 250                 255 aaa tta caa ctt tca gct gct gca aat gaa gat aca gta aac gta aat   912
Lys Leu Gln Leu Ser Ala Ala Ala Asn Glu Asp Thr Val Asn Val Asn
        260                 265                 270 act gta cgt atc tat aaa gtg gac ggt aac att cca ttt gcc ctt aat   960
Thr Val Arg Ile Tyr Lys Val Asp Gly Asn Ile Pro Phe Ala Leu Asn
275                 280                 285                 290 acg gca gat gtt tct tta tct aca gac gga aaa act atc act gtg gat  1008
Thr Ala Asp Val Ser Leu Ser Thr Asp Gly Lys Thr Ile Thr Val Asp
                295                 300                 305 gct tca act cca ttc gaa aat aat acg gag tat aaa gta gta gtt aaa  1056
Ala Ser Thr Pro Phe Glu Asn Asn Thr Glu Tyr Lys Val Val Val Lys
        310                 315                 320 ggt att aaa gac aaa aat ggc aaa gaa ttt aaa gaa gat gca ttc act  1104
Gly Ile Lys Asp Lys Asn Gly Lys Glu Phe Lys Glu Asp Ala Phe Thr
        325                 330                 335 ttc aag ctt cga aat gat gct gta gtt act caa gtg ttt gga act aat  1152
Phe Lys Leu Arg Asn Asp Ala Val Val Thr Gln Val Phe Gly Thr Asn
        340                 345                 350 gta aca aac aac act tct gta aac tta gca gca ggt act ttc gac act  1200
Val Thr Asn Asn Thr Ser Val Asn Leu Ala Ala Gly Thr Phe Asp Thr
355                 360                 365                 370 gac gat act tta aca gta gta ttt gat aag ttg tta gca cct gaa act  1248
Asp Asp Thr Leu Thr Val Val Phe Asp Lys Leu Leu Ala Pro Glu Thr
                375                 380                 385 gta aac agc tcg aac gtt act att aca gat gtt gaa act gga aaa cgc  1296
Val Asn Ser Ser Asn Val Thr Ile Thr Asp Val Glu Thr Gly Lys Arg
```

-continued

```
                   390                     395                       400
att cca gta att gca tct act tct ggt tct aca att act att acg tta       1344
Ile Pro Val Ile Ala Ser Thr Ser Gly Ser Thr Ile Thr Ile Thr Leu
        405                     410                     415 aaa gaa gcg tta gta act ggt aaa caa tat aaa ctt gct atc aat aat       1392
Lys Glu Ala Leu Val Thr Gly Lys Gln Tyr Lys Leu Ala Ile Asn Asn
420                     425                     430 gtt aaa aca tta act ggt tac aat gca gaa gct tac gag tta gtg ttc       1440
Val Lys Thr Leu Thr Gly Tyr Asn Ala Glu Ala Tyr Glu Leu Val Phe
435                     440                     445                 450 act gca aac gca tca gca cca act gtt gct acc gct cct act act tta       1488
Thr Ala Asn Ala Ser Ala Pro Thr Val Ala Thr Ala Pro Thr Thr Leu
                    455                     460                 465 ggt ggt aca act tta tct act ggt tct ctt aca aca aat gtt tgg ggt       1536
Gly Gly Thr Thr Leu Ser Thr Gly Ser Leu Thr Thr Asn Val Trp Gly
                470                     475                 480 aaa ttg gct ggt ggt gtg aat gaa gct gga act tat tat cct ggt ctt      1584
Lys Leu Ala Gly Gly Val Asn Glu Ala Gly Thr Tyr Tyr Pro Gly Leu
            485                     490                 495 caa ttc aca aca acg ttt gct act aag tta gac gaa tct act tta gct       1632
Gln Phe Thr Thr Thr Phe Ala Thr Lys Leu Asp Glu Ser Thr Leu Ala
        500                     505                     510 gat aac ttt gta tta gtt gaa aaa gaa tct ggt aca gtt gtt gct tct       1680
Asp Asn Phe Val Leu Val Glu Lys Glu Ser Gly Thr Val Val Ala Ser
515                     520                     525             530 gaa cta aaa tat aat gca gac gct aaa atg gta act tta gtg cca aaa       1728
Glu Leu Lys Tyr Asn Ala Asp Ala Lys Met Val Thr Leu Val Pro Lys
                535                     540                 545 gcg gac ctt aaa gaa aat aca atc tat caa atc aaa att aaa aaa ggc       1776
Ala Asp Leu Lys Glu Asn Thr Ile Tyr Gln Ile Lys Ile Lys Lys Gly
            550                     555                 560 ttg aag tcc gat aaa ggt att gaa tta ggc act gtt aac gag aaa aca       1824
Leu Lys Ser Asp Lys Gly Ile Glu Leu Gly Thr Val Asn Glu Lys Thr
        565                     570                 575 tat gag ttc aaa act caa gac tta act gct cct aca gtt att agc gta       1872
Tyr Glu Phe Lys Thr Gln Asp Leu Thr Ala Pro Thr Val Ile Ser Val
    580                     585                     590 acg tct aaa aat ggc gac gct gga tta aaa gta act gaa gct caa gaa       1920
Thr Ser Lys Asn Gly Asp Ala Gly Leu Lys Val Thr Glu Ala Gln Glu
595                     600                     605             610 ttt act gtg aag ttc tca gag aat tta aat aca ttt aat gct aca acc       1968
Phe Thr Val Lys Phe Ser Glu Asn Leu Asn Thr Phe Asn Ala Thr Thr
                615                     620                 625 gtt tcg ggt agc aca atc aca tac ggt caa gtt gct gta gta aaa gcg       2016
Val Ser Gly Ser Thr Ile Thr Tyr Gly Gln Val Ala Val Val Lys Ala
            630                     635                 640 ggt gca aac tta tct gct ctt aca gca agt gac atc att cca gct agt       2064
Gly Ala Asn Leu Ser Ala Leu Thr Ala Ser Asp Ile Ile Pro Ala Ser
        645                     650                 655 gtt gaa gcg gtt act ggt caa gat gga aca tac aaa gtg aaa gtt gct       2112
Val Glu Ala Val Thr Gly Gln Asp Gly Thr Tyr Lys Val Lys Val Ala
    660                     665                     670 gct aac caa tta gaa cgt aac caa ggg tac aaa tta gta gtg ttc ggt       2160
Ala Asn Gln Leu Glu Arg Asn Gln Gly Tyr Lys Leu Val Val Phe Gly
675                     680                     685             690 aaa ggt gca aca gct cct gtt aaa gat gct gca aat gca aat act tta       2208
Lys Gly Ala Thr Ala Pro Val Lys Asp Ala Ala Asn Ala Asn Thr Leu
                695                     700                 705 gca act aac tat atc tat aca ttt aca act gaa ggt caa gac gta aca       2256
```

```
                                                -continued

Ala Thr Asn Tyr Ile Tyr Thr Phe Thr Thr Glu Gly Gln Asp Val Thr
        710                 715                 720 gca cca acg gtt aca aaa gta ttc aaa ggt gat tct tta aaa gac gct      2304
Ala Pro Thr Val Thr Lys Val Phe Lys Gly Asp Ser Leu Lys Asp Ala
            725                 730                 735 gat gca gtt act aca ctt acg aac gtt gat gca ggt caa aaa ttc act      2352
Asp Ala Val Thr Thr Leu Thr Asn Val Asp Ala Gly Gln Lys Phe Thr
        740                 745                 750 atc caa ttt agc gaa gaa tta aaa act tct agt ggt tct tta gtg ggt      2400
Ile Gln Phe Ser Glu Glu Leu Lys Thr Ser Ser Gly Ser Leu Val Gly
755                 760                 765                 770 ggc aaa gta act gtc gag aaa tta aca aac aac gga tgg gta gat gct      2448
Gly Lys Val Thr Val Glu Lys Leu Thr Asn Asn Gly Trp Val Asp Ala
                775                 780                 785 ggt act gga aca act gta tca gtt gct cct aag aca gat gca aat ggt      2496
Gly Thr Gly Thr Thr Val Ser Val Ala Pro Lys Thr Asp Ala Asn Gly
        790                 795                 800 aaa gta aca gct gct gtg gtt aca tta act ggt ctt gac aat aac gac      2544
Lys Val Thr Ala Ala Val Val Thr Leu Thr Gly Leu Asp Asn Asn Asp
            805                 810                 815 aaa gat gcg aaa ttg cgt ctg gta gta gat aag tct tct act gat gga      2592
Lys Asp Ala Lys Leu Arg Leu Val Val Asp Lys Ser Ser Thr Asp Gly
820                 825                 830 att gct gat gta gct ggt aat gta att aag gaa aaa gat att tta att      2640
Ile Ala Asp Val Ala Gly Asn Val Ile Lys Glu Lys Asp Ile Leu Ile
835                 840                 845                 850 cgt tac aac agc tgg aga cac act gta gct tct gtg aaa gct gct gct      2688
Arg Tyr Asn Ser Trp Arg His Thr Val Ala Ser Val Lys Ala Ala Ala
                855                 860                 865 gac aaa gat ggt caa aac gct tct gct gca ttc cca aca agc act gca      2736
Asp Lys Asp Gly Gln Asn Ala Ser Ala Ala Phe Pro Thr Ser Thr Ala
        870                 875                 880 att gat aca act aag agc tta tta gtt gaa ttc aat gaa act gat tta      2784
Ile Asp Thr Thr Lys Ser Leu Leu Val Glu Phe Asn Glu Thr Asp Leu
            885                 890                 895 gcg gaa gtt aaa cct gag aac atc gtt gtt aaa gat gca gca ggt aat      2832
Ala Glu Val Lys Pro Glu Asn Ile Val Val Lys Asp Ala Ala Gly Asn
900                 905                 910 gcg gta gct ggt act gta aca gca tta gac ggt tct aca aat aaa ttt      2880
Ala Val Ala Gly Thr Val Thr Ala Leu Asp Gly Ser Thr Asn Lys Phe
915                 920                 925                 930 gta ttc act cca tct caa gaa tta aaa gct ggt aca gtt tac tct gta      2928
Val Phe Thr Pro Ser Gln Glu Leu Lys Ala Gly Thr Val Tyr Ser Val
                935                 940                 945 aca att gac ggt gtg aga gat aaa gta ggt aac aca atc tct aaa tac      2976
Thr Ile Asp Gly Val Arg Asp Lys Val Gly Asn Thr Ile Ser Lys Tyr
        950                 955                 960 att act tcg ttc aag act gta tct gcg aat cca acg tta tct tca atc      3024
Ile Thr Ser Phe Lys Thr Val Ser Ala Asn Pro Thr Leu Ser Ser Ile
            965                 970                 975 agc att gct gac ggt gca gtt aac gtt gac cgt tct aaa aca att aca      3072
Ser Ile Ala Asp Gly Ala Val Asn Val Asp Arg Ser Lys Thr Ile Thr
980                 985                 990 att gaa ttc agc gat tca  gtt cca aac cca aca  atc act ctt aag        3117
Ile Glu Phe Ser Asp Ser  Val Pro Asn Pro Thr  Ile Thr Leu Lys
995                      1000                  1005 aag  gct gac gga act tca  ttt act aat tac act  tta gta aat gta      3162
Lys  Ala Asp Gly Thr Ser  Phe Thr Asn Tyr Thr  Leu Val Asn Val
1010                      1015                  1020
```

```
aat aat gaa aat aaa aca tac aaa att gta ttc cac aaa ggt gta    3207
Asn Asn Glu Asn Lys Thr Tyr Lys Ile Val Phe His Lys Gly Val
1025                1030                1035 aca ctt gac gag ttt act caa tat gag tta gca gtt tca aaa gat    3252
Thr Leu Asp Glu Phe Thr Gln Tyr Glu Leu Ala Val Ser Lys Asp
1040                1045                1050 ttt caa act ggt act gat att gat agc aaa gtt aca ttc atc aca    3297
Phe Gln Thr Gly Thr Asp Ile Asp Ser Lys Val Thr Phe Ile Thr
1055                1060                1065 ggt tct gtt gct act gac gaa gta aaa cct gct cta gta ggc gtt    3342
Gly Ser Val Ala Thr Asp Glu Val Lys Pro Ala Leu Val Gly Val
1070                1075                1080 ggt tca tgg aat gga aca agc tat act cag gat gct gca gca aca    3387
Gly Ser Trp Asn Gly Thr Ser Tyr Thr Gln Asp Ala Ala Ala Thr
1085                1090                1095 cga ctt cgg tct gta gct gac ttc gtt gcg gag cca gtt gcc ctt    3432
Arg Leu Arg Ser Val Ala Asp Phe Val Ala Glu Pro Val Ala Leu
1100                1105                1110 caa ttc tca gaa ggt atc gat tta acg aat gca act gtg aca gta    3477
Gln Phe Ser Glu Gly Ile Asp Leu Thr Asn Ala Thr Val Thr Val
1115                1120                1125 aca aat att act gat gat aaa act gtt gaa gtt att tca aaa gag    3522
Thr Asn Ile Thr Asp Asp Lys Thr Val Glu Val Ile Ser Lys Glu
1130                1135                1140 agt gta gac gca gac cat gat gca ggt gct act aag gag aca tta    3567
Ser Val Asp Ala Asp His Asp Ala Gly Ala Thr Lys Glu Thr Leu
1145                1150                1155 gta att aac aca gtt act cct tta gta ctt gat aac agc aag act    3612
Val Ile Asn Thr Val Thr Pro Leu Val Leu Asp Asn Ser Lys Thr
1160                1165                1170 tat aag att gtt gta agt gga gtt aaa gat gca gca ggt aat gtt    3657
Tyr Lys Ile Val Val Ser Gly Val Lys Asp Ala Ala Gly Asn Val
1175                1180                1185 gca gat act att aca ttc tat att aag taa                        3687
Ala Asp Thr Ile Thr Phe Tyr Ile Lys
1190                1195
```

<210> SEQ ID NO 2
<211> LENGTH: 1228
<212> TYPE: PRT
<213> ORGANISM: Bacillus stearothermophilus

<400> SEQUENCE: 2

```
Met Asp Arg Lys Lys Ala Val Lys Leu Ala Thr Ala Ser Ala Ile Ala
-30                 -25                 -20                 -15

Ala Ser Ala Phe Val Ala Ala Asn Pro Asn Ala Ser Glu Ala Ala Thr
                -10                  -5                  -1   1

Asp Val Ala Thr Val Val Ser Gln Ala Lys Ala Gln Phe Lys Lys Ala
             5                  10                  15

Tyr Tyr Thr Tyr Ser His Thr Val Thr Glu Thr Gly Glu Phe Pro Asn
         20                  25                  30

Ile Asn Asp Val Tyr Ala Glu Tyr Asn Lys Ala Lys Lys Arg Tyr Arg
35                  40                  45                  50

Asp Ala Val Ala Leu Val Asn Lys Ala Gly Gly Ala Lys Lys Asp Ala
                55                  60                  65

Tyr Leu Ala Asp Leu Gln Lys Glu Tyr Glu Thr Tyr Val Phe Lys Ala
             70                  75                  80

Asn Pro Lys Ser Gly Glu Ala Arg Val Ala Thr Tyr Ile Asp Ala Tyr
         85                  90                  95
```

-continued

```
Asn Tyr Ala Thr Lys Leu Asp Glu Met Arg Gln Glu Leu Glu Ala Ala
    100                 105                 110
Val Gln Ala Lys Asp Leu Glu Lys Ala Glu Gln Tyr Tyr His Lys Ile
115                 120                 125                 130
Pro Tyr Glu Ile Lys Thr Arg Thr Val Ile Leu Asp Arg Val Tyr Gly
                135                 140                 145
Lys Thr Thr Arg Asp Leu Leu Arg Ser Thr Phe Lys Ala Lys Ala Gln
                150                 155                 160
Glu Leu Arg Asp Ser Leu Ile Tyr Asp Ile Thr Val Ala Met Lys Ala
            165                 170                 175
Arg Glu Val Gln Asp Ala Val Lys Ala Gly Asn Leu Asp Lys Ala Lys
        180                 185                 190
Ala Ala Val Asp Gln Ile Asn Gln Tyr Leu Pro Lys Val Thr Asp Ala
195                 200                 205                 210
Phe Lys Thr Glu Leu Thr Glu Val Ala Lys Lys Ala Leu Asp Ala Asp
                215                 220                 225
Glu Ala Ala Leu Thr Pro Lys Val Glu Ser Val Ser Ala Ile Asn Thr
            230                 235                 240
Gln Asn Lys Ala Val Glu Leu Thr Ala Val Pro Val Asn Gly Thr Leu
        245                 250                 255
Lys Leu Gln Leu Ser Ala Ala Ala Asn Glu Asp Thr Val Asn Val Asn
    260                 265                 270
Thr Val Arg Ile Tyr Lys Val Asp Gly Asn Ile Pro Phe Ala Leu Asn
275                 280                 285                 290
Thr Ala Asp Val Ser Leu Ser Thr Asp Gly Lys Thr Ile Thr Val Asp
                295                 300                 305
Ala Ser Thr Pro Phe Glu Asn Asn Thr Glu Tyr Lys Val Val Val Lys
            310                 315                 320
Gly Ile Lys Asp Lys Asn Gly Lys Glu Phe Lys Glu Asp Ala Phe Thr
        325                 330                 335
Phe Lys Leu Arg Asn Asp Ala Val Val Thr Gln Val Phe Gly Thr Asn
    340                 345                 350
Val Thr Asn Asn Thr Ser Val Asn Leu Ala Ala Gly Thr Phe Asp Thr
355                 360                 365                 370
Asp Asp Thr Leu Thr Val Val Phe Asp Lys Leu Leu Ala Pro Glu Thr
                375                 380                 385
Val Asn Ser Ser Asn Val Thr Ile Thr Asp Val Glu Thr Gly Lys Arg
            390                 395                 400
Ile Pro Val Ile Ala Ser Thr Ser Gly Ser Thr Ile Thr Ile Thr Leu
        405                 410                 415
Lys Glu Ala Leu Val Thr Gly Lys Gln Tyr Lys Leu Ala Ile Asn Asn
    420                 425                 430
Val Lys Thr Leu Thr Gly Tyr Asn Ala Glu Ala Tyr Glu Leu Val Phe
435                 440                 445                 450
Thr Ala Asn Ala Ser Ala Pro Thr Val Ala Thr Ala Pro Thr Thr Leu
                455                 460                 465
Gly Gly Thr Thr Leu Ser Thr Gly Ser Leu Thr Thr Asn Val Trp Gly
            470                 475                 480
Lys Leu Ala Gly Gly Val Asn Glu Ala Gly Thr Tyr Tyr Pro Gly Leu
        485                 490                 495
Gln Phe Thr Thr Thr Phe Ala Thr Lys Leu Asp Glu Ser Thr Leu Ala
    500                 505                 510
```

-continued

```
Asp Asn Phe Val Leu Val Glu Lys Glu Ser Gly Thr Val Val Ala Ser
515                 520                 525                 530

Glu Leu Lys Tyr Asn Ala Asp Ala Lys Met Val Thr Leu Val Pro Lys
            535                 540                 545

Ala Asp Leu Lys Glu Asn Thr Ile Tyr Gln Ile Lys Ile Lys Lys Gly
            550                 555                 560

Leu Lys Ser Asp Lys Gly Ile Glu Leu Gly Thr Val Asn Glu Lys Thr
            565                 570                 575

Tyr Glu Phe Lys Thr Gln Asp Leu Thr Ala Pro Thr Val Ile Ser Val
580                 585                 590

Thr Ser Lys Asn Gly Asp Ala Gly Leu Lys Val Thr Glu Ala Gln Glu
595                 600                 605                 610

Phe Thr Val Lys Phe Ser Glu Asn Leu Asn Thr Phe Asn Ala Thr Thr
                615                 620                 625

Val Ser Gly Ser Thr Ile Thr Tyr Gly Gln Val Ala Val Val Lys Ala
                630                 635                 640

Gly Ala Asn Leu Ser Ala Leu Thr Ala Ser Asp Ile Ile Pro Ala Ser
                645                 650                 655

Val Glu Ala Val Thr Gly Gln Asp Gly Thr Tyr Lys Val Lys Val Ala
660                 665                 670

Ala Asn Gln Leu Glu Arg Asn Gln Gly Tyr Lys Leu Val Val Phe Gly
675                 680                 685                 690

Lys Gly Ala Thr Ala Pro Val Lys Asp Ala Ala Asn Ala Asn Thr Leu
                695                 700                 705

Ala Thr Asn Tyr Ile Tyr Thr Phe Thr Thr Glu Gly Gln Asp Val Thr
                710                 715                 720

Ala Pro Thr Val Thr Lys Val Phe Lys Gly Asp Ser Leu Lys Asp Ala
                725                 730                 735

Asp Ala Val Thr Thr Leu Thr Asn Val Asp Ala Gly Gln Lys Phe Thr
                740                 745                 750

Ile Gln Phe Ser Glu Glu Leu Lys Thr Ser Ser Gly Ser Leu Val Gly
755                 760                 765                 770

Gly Lys Val Thr Val Glu Lys Leu Thr Asn Asn Gly Trp Val Asp Ala
                775                 780                 785

Gly Thr Gly Thr Thr Val Ser Val Ala Pro Lys Thr Asp Ala Asn Gly
                790                 795                 800

Lys Val Thr Ala Ala Val Thr Leu Thr Gly Leu Asp Asn Asn Asp
                805                 810                 815

Lys Asp Ala Lys Leu Arg Leu Val Val Asp Lys Ser Thr Asp Gly
820                 825                 830

Ile Ala Asp Val Ala Gly Asn Val Ile Lys Glu Lys Asp Ile Leu Ile
835                 840                 845                 850

Arg Tyr Asn Ser Trp Arg His Thr Val Ala Ser Val Lys Ala Ala Ala
                855                 860                 865

Asp Lys Asp Gly Gln Asn Ala Ser Ala Ala Phe Pro Thr Ser Thr Ala
                870                 875                 880

Ile Asp Thr Thr Lys Ser Leu Leu Val Glu Phe Asn Glu Thr Asp Leu
                885                 890                 895

Ala Glu Val Lys Pro Glu Asn Ile Val Lys Asp Ala Ala Gly Asn
        900                 905                 910

Ala Val Ala Gly Thr Val Thr Ala Leu Asp Gly Ser Thr Asn Lys Phe
915                 920                 925                 930

Val Phe Thr Pro Ser Gln Glu Leu Lys Ala Gly Thr Val Tyr Ser Val
```

-continued

```
                      935                 940                 945
Thr Ile Asp Gly Val Arg Asp Lys Val Gly Asn Thr Ile Ser Lys Tyr
                950                 955                 960
Ile Thr Ser Phe Lys Thr Val Ser Ala Asn Pro Thr Leu Ser Ser Ile
                965                 970                 975
Ser Ile Ala Asp Gly Ala Val Asn Val Asp Arg Ser Lys Thr Ile Thr
            980                 985                 990
Ile Glu Phe Ser Asp Ser  Val Pro Asn Pro Thr  Ile Thr Leu Lys
995                 1000                1005
Lys Ala Asp Gly Thr Ser  Phe Thr Asn Tyr Thr  Leu Val Asn Val
1010                1015                1020
Asn Asn Glu Asn Lys Thr  Tyr Lys Ile Val Phe  His Lys Gly Val
1025                1030                1035
Thr Leu Asp Glu Phe Thr  Gln Tyr Glu Leu Ala  Val Ser Lys Asp
1040                1045                1050
Phe Gln Thr Gly Thr Asp  Ile Asp Ser Lys Val  Thr Phe Ile Thr
1055                1060                1065
Gly Ser Val Ala Thr Asp  Glu Val Lys Pro Ala  Leu Val Gly Val
1070                1075                1080
Gly Ser Trp Asn Gly Thr  Ser Tyr Thr Gln Asp  Ala Ala Ala Thr
1085                1090                1095
Arg Leu Arg Ser Val Ala  Asp Phe Val Ala Glu  Pro Val Ala Leu
1100                1105                1110
Gln Phe Ser Glu Gly Ile  Asp Leu Thr Asn Ala  Thr Val Thr Val
1115                1120                1125
Thr Asn Ile Thr Asp Asp  Lys Thr Val Glu Val  Ile Ser Lys Glu
1130                1135                1140
Ser Val Asp Ala Asp His  Asp Ala Gly Ala Thr  Lys Glu Thr Leu
1145                1150                1155
Val Ile Asn Thr Val Thr  Pro Leu Val Leu Asp  Asn Ser Lys Thr
1160                1165                1170
Tyr Lys Ile Val Val Ser  Gly Val Lys Asp Ala  Ala Gly Asn Val
1175                1180                1185
Ala Asp Thr Ile Thr Phe  Tyr Ile Lys
1190                1195

<210> SEQ ID NO 3
<211> LENGTH: 2766
<212> TYPE: DNA
<213> ORGANISM: Bacillus stearothermophilus
<220> FEATURE:
<221> NAME/KEY: CDS
<222> LOCATION: (1)..(2763)
<223> OTHER INFORMATION:
<221> NAME/KEY: sig_peptide
<222> LOCATION: (1)..(93)
<223> OTHER INFORMATION:
<221> NAME/KEY: mat_peptide
<222> LOCATION: (94)..(2763)
<223> OTHER INFORMATION:

<400> SEQUENCE: 3 atg gct tat caa cct aag tcc tat cgc aag ttt gtt gcg aca act gca      48
Met Ala Tyr Gln Pro Lys Ser Tyr Arg Lys Phe Val Ala Thr Thr Ala
    -30                 -25                 -20 aca gct gcc atg gta gca tct gcg gta gct cct gta gta tct gca gca      96
Thr Ala Ala Met Val Ala Ser Ala Val Ala Pro Val Val Ser Ala Ala
-15                 -10                 -5                 -1   1
```

-continued

| | | | | | | | | | | | | | | | | |
|---|---|---|---|---|---|---|---|---|---|---|---|---|---|---|---|---|
| agc | ttc | aca | gat | gtt | gcg | ccg | caa | tat | aaa | gat | gcg | atc | gat | ttc | tta | 144 |
| Ser | Phe | Thr | Asp | Val | Ala | Pro | Gln | Tyr | Lys | Asp | Ala | Ile | Asp | Phe | Leu | |
| | | | 5 | | | | | 10 | | | | | 15 | | | |
| gta | tca | act | ggt | gca | aca | aaa | ggt | aaa | aca | gaa | aca | aaa | ttc | ggc | gtt | 192 |
| Val | Ser | Thr | Gly | Ala | Thr | Lys | Gly | Lys | Thr | Glu | Thr | Lys | Phe | Gly | Val | |
| | | | 20 | | | | | 25 | | | | | 30 | | | |
| tac | gat | gaa | atc | act | cgt | cta | gat | gcg | gca | gtt | att | ctt | gca | aga | gta | 240 |
| Tyr | Asp | Glu | Ile | Thr | Arg | Leu | Asp | Ala | Ala | Val | Ile | Leu | Ala | Arg | Val | |
| | 35 | | | | | | 40 | | | | | 45 | | | | |
| tta | aaa | cta | gac | gtt | gac | aac | gca | aaa | gac | gca | ggc | ttc | aca | gat | gtg | 288 |
| Leu | Lys | Leu | Asp | Val | Asp | Asn | Ala | Lys | Asp | Ala | Gly | Phe | Thr | Asp | Val | |
| 50 | | | | | 55 | | | | | 60 | | | | | 65 | |
| cca | aaa | gac | cgt | gca | aaa | tac | gtc | aac | gcg | ctt | gta | gaa | gct | ggc | gta | 336 |
| Pro | Lys | Asp | Arg | Ala | Lys | Tyr | Val | Asn | Ala | Leu | Val | Glu | Ala | Gly | Val | |
| | | | 70 | | | | | 75 | | | | | 80 | | | |
| tta | aac | ggt | aaa | gca | cct | ggc | aaa | ttt | ggt | gca | tac | gac | cca | tta | act | 384 |
| Leu | Asn | Gly | Lys | Ala | Pro | Gly | Lys | Phe | Gly | Ala | Tyr | Asp | Pro | Leu | Thr | |
| | | | 85 | | | | | 90 | | | | | 95 | | | |
| cgc | gtt | gaa | atg | gca | aaa | atc | atc | gcg | aac | cgt | tac | aaa | tta | aaa | gct | 432 |
| Arg | Val | Glu | Met | Ala | Lys | Ile | Ile | Ala | Asn | Arg | Tyr | Lys | Leu | Lys | Ala | |
| | | | 100 | | | | | 105 | | | | | 110 | | | |
| gac | gat | gta | aaa | ctt | cca | ttc | act | gat | gta | aac | gat | aca | tgg | gca | cca | 480 |
| Asp | Asp | Val | Lys | Leu | Pro | Phe | Thr | Asp | Val | Asn | Asp | Thr | Trp | Ala | Pro | |
| | 115 | | | | | | 120 | | | | | 125 | | | | |
| tac | gta | aaa | gcg | ctt | tat | aaa | tac | gaa | gta | acc | aaa | agg | tta | aaa | cac | 528 |
| Tyr | Val | Lys | Ala | Leu | Tyr | Lys | Tyr | Glu | Val | Thr | Lys | Arg | Leu | Lys | His | |
| 130 | | | | | 135 | | | | | 140 | | | | | 145 | |
| caa | caa | gct | tcg | gtg | cat | acc | aaa | aac | atc | act | ctg | cgt | gac | ttt | gcg | 576 |
| Gln | Gln | Ala | Ser | Val | His | Thr | Lys | Asn | Ile | Thr | Leu | Arg | Asp | Phe | Ala | |
| | | | 150 | | | | | 155 | | | | | 160 | | | |
| caa | ttt | gta | tat | aga | gcg | gtg | aat | att | aat | gca | gtg | cca | gaa | ata | gtt | 624 |
| Gln | Phe | Val | Tyr | Arg | Ala | Val | Asn | Ile | Asn | Ala | Val | Pro | Glu | Ile | Val | |
| | | | 165 | | | | | 170 | | | | | 175 | | | |
| gaa | gta | act | gcg | gtt | aat | tcg | act | aca | gtg | aaa | gta | aca | ttc | aat | acg | 672 |
| Glu | Val | Thr | Ala | Val | Asn | Ser | Thr | Thr | Val | Lys | Val | Thr | Phe | Asn | Thr | |
| | | | 180 | | | | | 185 | | | | | 190 | | | |
| caa | att | gct | gat | gtt | gat | ttc | aca | aat | ttt | gct | atc | gat | aac | ggt | tta | 720 |
| Gln | Ile | Ala | Asp | Val | Asp | Phe | Thr | Asn | Phe | Ala | Ile | Asp | Asn | Gly | Leu | |
| | 195 | | | | | | 200 | | | | | 205 | | | | |
| act | gtt | act | aaa | gca | act | ctt | tct | cgt | gat | aaa | aaa | tcc | gta | gag | gtt | 768 |
| Thr | Val | Thr | Lys | Ala | Thr | Leu | Ser | Arg | Asp | Lys | Lys | Ser | Val | Glu | Val | |
| 210 | | | | | 215 | | | | | 220 | | | | | 225 | |
| gtg | gta | aat | aaa | ccg | ttt | act | cgt | aat | cag | gaa | tat | aca | att | aca | gcg | 816 |
| Val | Val | Asn | Lys | Pro | Phe | Thr | Arg | Asn | Gln | Glu | Tyr | Thr | Ile | Thr | Ala | |
| | | | 230 | | | | | 235 | | | | | 240 | | | |
| aca | ggc | att | aaa | aat | tta | aaa | ggc | gag | acc | gct | aag | gaa | tta | act | ggt | 864 |
| Thr | Gly | Ile | Lys | Asn | Leu | Lys | Gly | Glu | Thr | Ala | Lys | Glu | Leu | Thr | Gly | |
| | | | 245 | | | | | 250 | | | | | 255 | | | |
| aag | ttt | gtt | tgg | tct | gtt | caa | gat | gcg | gta | act | gtt | gca | cta | aat | aat | 912 |
| Lys | Phe | Val | Trp | Ser | Val | Gln | Asp | Ala | Val | Thr | Val | Ala | Leu | Asn | Asn | |
| | | | 260 | | | | | 265 | | | | | 270 | | | |
| agt | tcg | ctt | aaa | gtt | gga | gag | gaa | tct | ggt | tta | act | gta | aaa | gat | cag | 960 |
| Ser | Ser | Leu | Lys | Val | Gly | Glu | Glu | Ser | Gly | Leu | Thr | Val | Lys | Asp | Gln | |
| | | | 275 | | | | | 280 | | | | | 285 | | | |
| gat | ggc | aaa | gat | gtt | gta | ggt | gct | aaa | gta | gaa | ctt | act | tct | tct | aat | 1008 |
| Asp | Gly | Lys | Asp | Val | Val | Gly | Ala | Lys | Val | Glu | Leu | Thr | Ser | Ser | Asn | |
| 290 | | | | | 295 | | | | | 300 | | | | | 305 | |
| act | aat | att | gtt | gta | gtt | tca | agt | ggc | gaa | gta | tca | gta | tct | gct | gct | 1056 |
| Thr | Asn | Ile | Val | Val | Val | Ser | Ser | Gly | Glu | Val | Ser | Val | Ser | Ala | Ala | |
| | | | 310 | | | | | 315 | | | | | 320 | | | |

```
aaa gtt aca gct gta aaa ccg gga aca gct gat gtt act gca aaa gtt    1104
Lys Val Thr Ala Val Lys Pro Gly Thr Ala Asp Val Thr Ala Lys Val
            325                 330                 335 aca tta cca gat ggt gtt gta cta aca aat aca ttt aaa gtg aca gtt    1152
Thr Leu Pro Asp Gly Val Val Leu Thr Asn Thr Phe Lys Val Thr Val
        340                 345                 350 aca gaa gtg cct gtg caa gta caa aat caa gga ttt act tta gtt gat    1200
Thr Glu Val Pro Val Gln Val Gln Asn Gln Gly Phe Thr Leu Val Asp
    355                 360                 365 aat ctt tct aat gct cca cag aat aca gtt gca ttt aac aaa gct gag    1248
Asn Leu Ser Asn Ala Pro Gln Asn Thr Val Ala Phe Asn Lys Ala Glu
370                 375                 380                 385 aaa gta act tca atg ttt gct gga gaa act aaa aca gtt gca atg tat    1296
Lys Val Thr Ser Met Phe Ala Gly Glu Thr Lys Thr Val Ala Met Tyr
            390                 395                 400 gat act aaa aac ggt gat cct gaa act aaa cct gtt gat ttc aaa gat    1344
Asp Thr Lys Asn Gly Asp Pro Glu Thr Lys Pro Val Asp Phe Lys Asp
        405                 410                 415 gca act gta cgt tca tta aat cca att att gca aca gct gct att aat    1392
Ala Thr Val Arg Ser Leu Asn Pro Ile Ile Ala Thr Ala Ala Ile Asn
    420                 425                 430 ggt agt gag ctc ctt gtc aca gct aat gct ggc caa tct gga aaa gct    1440
Gly Ser Glu Leu Leu Val Thr Ala Asn Ala Gly Gln Ser Gly Lys Ala
435                 440                 445 tca ttt gaa gta aca ttt aaa gat aat aca aaa aga aca ttt aca gtt    1488
Ser Phe Glu Val Thr Phe Lys Asp Asn Thr Lys Arg Thr Phe Thr Val
450                 455                 460                 465 gat gtg aaa aaa gac cct gta tta caa gat att aaa gta gat gca act    1536
Asp Val Lys Lys Asp Pro Val Leu Gln Asp Ile Lys Val Asp Ala Thr
            470                 475                 480 tct gtt aaa ctt tcc gat gaa gct gtt ggc ggc ggg gaa gtt gaa gga    1584
Ser Val Lys Leu Ser Asp Glu Ala Val Gly Gly Gly Glu Val Glu Gly
        485                 490                 495 gtt aac caa aaa acg att aaa gta agt gca gtt gac caa tac ggt aaa    1632
Val Asn Gln Lys Thr Ile Lys Val Ser Ala Val Asp Gln Tyr Gly Lys
    500                 505                 510 gaa att aaa ttt ggt aca aaa ggt aaa gtt act gtt aca act aat aca    1680
Glu Ile Lys Phe Gly Thr Lys Gly Lys Val Thr Val Thr Thr Asn Thr
515                 520                 525 gaa gga cta gtt att aaa aat gta aat agc gat aat aca att gac ttt    1728
Glu Gly Leu Val Ile Lys Asn Val Asn Ser Asp Asn Thr Ile Asp Phe
530                 535                 540                 545 gat agc ggc aat agt gca act gac caa ttt gtt gtc gtt gca aca aaa    1776
Asp Ser Gly Asn Ser Ala Thr Asp Gln Phe Val Val Val Ala Thr Lys
            550                 555                 560 gac aaa att gtc aat ggt aaa gta gaa gtt aaa tat ttc aaa aat gct    1824
Asp Lys Ile Val Asn Gly Lys Val Glu Val Lys Tyr Phe Lys Asn Ala
        565                 570                 575 agt gac aca aca cca act tca act aaa aca att act gtt aat gta gtg    1872
Ser Asp Thr Thr Pro Thr Ser Thr Lys Thr Ile Thr Val Asn Val Val
    580                 585                 590 aat gta aaa gct gac gct aca cca gta gga tta gat att gta gca cct    1920
Asn Val Lys Ala Asp Ala Thr Pro Val Gly Leu Asp Ile Val Ala Pro
595                 600                 605 tct gaa att gat gtg aat gct cca aac act gct tct act gca gat gtt    1968
Ser Glu Ile Asp Val Asn Ala Pro Asn Thr Ala Ser Thr Ala Asp Val
610                 615                 620                 625 gat ttt att aat ttc gaa agt gtt gag att tat aca ctc gat tct aat    2016
Asp Phe Ile Asn Phe Glu Ser Val Glu Ile Tyr Thr Leu Asp Ser Asn
```

-continued

```
            630                 635                 640 ggt aac cgt ctt aaa aaa gtt act cca act gca act aca ctt gta ggt      2064
Gly Asn Arg Leu Lys Lys Val Thr Pro Thr Ala Thr Thr Leu Val Gly
            645                 650                 655 act aat gat tat gtt gaa gtt aat ggg aat gta tta caa ttc aag ggt      2112
Thr Asn Asp Tyr Val Glu Val Asn Gly Asn Val Leu Gln Phe Lys Gly
        660                 665                 670 aac gat gaa tta acg cta tta act tct tct agt aca gta aac gtt gat      2160
Asn Asp Glu Leu Thr Leu Leu Thr Ser Ser Ser Thr Val Asn Val Asp
    675                 680                 685 gta aca gct gat gga att aca aaa cgt att cca gta aaa tat atc aac      2208
Val Thr Ala Asp Gly Ile Thr Lys Arg Ile Pro Val Lys Tyr Ile Asn
690                 695                 700                 705 tct gca agt gta cct gcc agt gca aca gta gca aca agt cct gtt act      2256
Ser Ala Ser Val Pro Ala Ser Ala Thr Val Ala Thr Ser Pro Val Thr
                710                 715                 720 gtt aag ctt aat tca agt gat aat gat tta aca ttt gaa gaa tta ata      2304
Val Lys Leu Asn Ser Ser Asp Asn Asp Leu Thr Phe Glu Glu Leu Ile
            725                 730                 735 ttc ggt gta att gac cct aca caa tta gtc aaa gat gaa gac atc aac      2352
Phe Gly Val Ile Asp Pro Thr Gln Leu Val Lys Asp Glu Asp Ile Asn
        740                 745                 750 gaa ttt att gca gtt tca aaa gcg gct aaa aat gat gga tat ttg tat      2400
Glu Phe Ile Ala Val Ser Lys Ala Ala Lys Asn Asp Gly Tyr Leu Tyr
    755                 760                 765 aat aaa ccg ctt gta acg gtt aaa gat gca tca gga aaa gtt att cca      2448
Asn Lys Pro Leu Val Thr Val Lys Asp Ala Ser Gly Lys Val Ile Pro
770                 775                 780                 785 aca ggt gca aat gtt tac ggt cta aat cat gat gca act aac gga aac      2496
Thr Gly Ala Asn Val Tyr Gly Leu Asn His Asp Ala Thr Asn Gly Asn
                790                 795                 800 att tgg ttt gat gag gaa caa gct ggc tta gct aaa aaa ttt agt gat      2544
Ile Trp Phe Asp Glu Glu Gln Ala Gly Leu Ala Lys Lys Phe Ser Asp
            805                 810                 815 gta cat ttt gat gtt gat ttt tca tta gct aac gtt gta aaa act ggt      2592
Val His Phe Asp Val Asp Phe Ser Leu Ala Asn Val Val Lys Thr Gly
        820                 825                 830 agc ggt aca gtt tct tca tcg cca tca tta tct gac gca att caa ctt      2640
Ser Gly Thr Val Ser Ser Ser Pro Ser Leu Ser Asp Ala Ile Gln Leu
    835                 840                 845 act aat tca ggc gat gca gta tcg ttt aca tta gtt atc aaa tca att      2688
Thr Asn Ser Gly Asp Ala Val Ser Phe Thr Leu Val Ile Lys Ser Ile
850                 855                 860                 865 tat gtt aaa ggc gca gat aaa gat gat aat aac tta ctt gca gcc cct      2736
Tyr Val Lys Gly Ala Asp Lys Asp Asp Asn Asn Leu Leu Ala Ala Pro
                870                 875                 880 gtt tct gtc aat gtg act gtg aca aaa taa                              2766
Val Ser Val Asn Val Thr Val Thr Lys
            885                 890

<210> SEQ ID NO 4
<211> LENGTH: 921
<212> TYPE: PRT
<213> ORGANISM: Bacillus stearothermophilus

<400> SEQUENCE: 4

Met Ala Tyr Gln Pro Lys Ser Tyr Arg Lys Phe Val Ala Thr Thr Ala
1               5                   10                  15

Thr Ala Ala Met Val Ala Ser Ala Val Ala Pro Val Val Ser Ala Ala
            20                  25                  30
```

-continued

```
Ser Phe Thr Asp Val Ala Pro Gln Tyr Lys Asp Ala Ile Asp Phe Leu
        35                  40                  45
Val Ser Thr Gly Ala Thr Lys Gly Lys Thr Glu Thr Lys Phe Gly Val
 50                  55                  60
Tyr Asp Glu Ile Thr Arg Leu Asp Ala Val Ile Leu Ala Arg Val
 65                  70                  75                  80
Leu Lys Leu Asp Val Asp Asn Ala Lys Asp Ala Gly Phe Thr Asp Val
                 85                  90                  95
Pro Lys Asp Arg Ala Lys Tyr Val Asn Ala Leu Val Glu Ala Gly Val
            100                 105                 110
Leu Asn Gly Lys Ala Pro Gly Lys Phe Gly Ala Tyr Asp Pro Leu Thr
            115                 120                 125
Arg Val Glu Met Ala Lys Ile Ile Ala Asn Arg Tyr Lys Leu Lys Ala
            130                 135                 140
Asp Asp Val Lys Leu Pro Phe Thr Asp Val Asn Asp Thr Trp Ala Pro
145                 150                 155                 160
Tyr Val Lys Ala Leu Tyr Lys Tyr Glu Val Thr Lys Arg Leu Lys His
                165                 170                 175
Gln Gln Ala Ser Val His Thr Lys Asn Ile Thr Leu Arg Asp Phe Ala
            180                 185                 190
Gln Phe Val Tyr Arg Ala Val Asn Ile Asn Ala Val Pro Glu Ile Val
            195                 200                 205
Glu Val Thr Ala Val Asn Ser Thr Thr Val Lys Val Thr Phe Asn Thr
            210                 215                 220
Gln Ile Ala Asp Val Asp Phe Thr Asn Phe Ala Ile Asp Asn Gly Leu
225                 230                 235                 240
Thr Val Thr Lys Ala Thr Leu Ser Arg Asp Lys Lys Ser Val Glu Val
                245                 250                 255
Val Val Asn Lys Pro Phe Thr Arg Asn Gln Glu Tyr Thr Ile Thr Ala
            260                 265                 270
Thr Gly Ile Lys Asn Leu Lys Gly Glu Thr Ala Lys Glu Leu Thr Gly
            275                 280                 285
Lys Phe Val Trp Ser Val Gln Asp Ala Val Thr Val Ala Leu Asn Asn
            290                 295                 300
Ser Ser Leu Lys Val Gly Glu Glu Ser Gly Leu Thr Val Lys Asp Gln
305                 310                 315                 320
Asp Gly Lys Asp Val Val Gly Ala Lys Val Glu Leu Thr Ser Ser Asn
                325                 330                 335
Thr Asn Ile Val Val Ser Ser Gly Glu Val Ser Val Ser Ala Ala
            340                 345                 350
Lys Val Thr Ala Val Lys Pro Gly Thr Ala Asp Val Thr Ala Lys Val
            355                 360                 365
Thr Leu Pro Asp Gly Val Val Leu Thr Asn Thr Phe Lys Val Thr Val
            370                 375                 380
Thr Glu Val Pro Val Gln Val Gln Asn Gln Gly Phe Thr Leu Val Asp
385                 390                 395                 400
Asn Leu Ser Asn Ala Pro Gln Asn Thr Val Ala Phe Asn Lys Ala Glu
                405                 410                 415
Lys Val Thr Ser Met Phe Ala Gly Glu Thr Lys Thr Val Ala Met Tyr
            420                 425                 430
Asp Thr Lys Asn Gly Asp Pro Glu Thr Lys Pro Val Asp Phe Lys Asp
            435                 440                 445
```

```
Ala Thr Val Arg Ser Leu Asn Pro Ile Ile Ala Thr Ala Ala Ile Asn
        450                 455                 460
Gly Ser Glu Leu Leu Val Thr Ala Asn Ala Gly Gln Ser Gly Lys Ala
465                 470                 475                 480
Ser Phe Glu Val Thr Phe Lys Asp Asn Thr Lys Arg Thr Phe Thr Val
                485                 490                 495
Asp Val Lys Lys Asp Pro Val Leu Gln Asp Ile Lys Val Asp Ala Thr
            500                 505                 510
Ser Val Lys Leu Ser Asp Glu Ala Val Gly Gly Glu Val Glu Gly
        515                 520                 525
Val Asn Gln Lys Thr Ile Lys Val Ser Ala Val Asp Gln Tyr Gly Lys
        530                 535                 540
Glu Ile Lys Phe Gly Thr Lys Gly Lys Val Thr Val Thr Thr Asn Thr
545                 550                 555                 560
Glu Gly Leu Val Ile Lys Asn Val Asn Ser Asp Asn Thr Ile Asp Phe
                565                 570                 575
Asp Ser Gly Asn Ser Ala Thr Asp Gln Phe Val Val Ala Thr Lys
            580                 585                 590
Asp Lys Ile Val Asn Gly Lys Val Glu Val Lys Tyr Phe Lys Asn Ala
        595                 600                 605
Ser Asp Thr Thr Pro Thr Ser Thr Lys Thr Ile Thr Val Asn Val Val
        610                 615                 620
Asn Val Lys Ala Asp Ala Thr Pro Val Gly Leu Asp Ile Val Ala Pro
625                 630                 635                 640
Ser Glu Ile Asp Val Asn Ala Pro Asn Thr Ala Ser Thr Ala Asp Val
                645                 650                 655
Asp Phe Ile Asn Phe Glu Ser Val Glu Ile Tyr Thr Leu Asp Ser Asn
                660                 665                 670
Gly Asn Arg Leu Lys Lys Val Thr Pro Thr Ala Thr Leu Val Gly
        675                 680                 685
Thr Asn Asp Tyr Val Glu Val Asn Gly Asn Val Leu Gln Phe Lys Gly
        690                 695                 700
Asn Asp Glu Leu Thr Leu Leu Thr Ser Ser Thr Val Asn Val Asp
705                 710                 715                 720
Val Thr Ala Asp Gly Ile Thr Lys Arg Ile Pro Val Lys Tyr Ile Asn
                725                 730                 735
Ser Ala Ser Val Pro Ala Ser Ala Thr Val Ala Thr Ser Pro Val Thr
            740                 745                 750
Val Lys Leu Asn Ser Ser Asp Asn Asp Leu Thr Phe Glu Glu Leu Ile
        755                 760                 765
Phe Gly Val Ile Asp Pro Thr Gln Leu Val Lys Asp Glu Asp Ile Asn
        770                 775                 780
Glu Phe Ile Ala Val Ser Lys Ala Ala Lys Asn Asp Gly Tyr Leu Tyr
785                 790                 795                 800
Asn Lys Pro Leu Val Thr Val Lys Asp Ala Ser Gly Lys Val Ile Pro
                805                 810                 815
Thr Gly Ala Asn Val Tyr Gly Leu Asn His Asp Ala Thr Asn Gly Asn
            820                 825                 830
Ile Trp Phe Asp Glu Glu Gln Ala Gly Leu Ala Lys Lys Phe Ser Asp
        835                 840                 845
Val His Phe Asp Val Asp Phe Ser Leu Ala Asn Val Val Lys Thr Gly
        850                 855                 860
Ser Gly Thr Val Ser Ser Ser Pro Ser Leu Ser Asp Ala Ile Gln Leu
```

-continued

```
            865                 870                 875                 880
Thr Asn Ser Gly Asp Ala Val Ser Phe Thr Leu Val Ile Lys Ser Ile
                885                 890                 895
Tyr Val Lys Gly Ala Asp Lys Asp Asp Asn Asn Leu Leu Ala Ala Pro
                900                 905                 910
Val Ser Val Asn Val Thr Val Thr Lys
                915                 920
```

COMPARTMENTALIZATION OF RECOMBINANT POLYPEPTIDES IN HOST CELLS

The present invention relates to host cells which contain at least two functional recombinant polypeptides, at least one of which is bound to a support, preferably in each case in different cell compartments, e.g. cytosol, cytoplasmic membrane, periplasm and outer membrane, and also to methods for preparing said host cells. The cells of the invention are particularly suited as bioreactors for carrying out enzymatic reaction cascades for which compartmentalization of individual enzymes is advantageous or necessary.

The use of living cells as "enzyme reactors" for preparing biological substances, e.g. polyhydroxy fatty acids, is of great importance for the biotechnological industry. To this end, it is common to introduce foreign genes into a host cell and to express said genes, in order to obtain in this manner a host cell with recombinant enzymes, which is capable of synthesizing a desired product. A disadvantage of known methods, however, was that the enzymes generated in the host cells by expression of the foreign genes were not stable, had too little activity or were present in too small an amount. Particular difficulties also stepped when carrying out multistage reactions in which substrates or products of one stage may have an adverse effect on other stages.

It was an object of the present invention to eliminate at least partially the problems of the prior art and to provide host cells which are capable of presenting functional recombinant polypeptides in a stable form and, in particular, of carrying out multistage enzyme reactions.

The object is achieved by providing a host cell comprising at least two functional recombinant polypeptides at least one of which is bound to a support.

Surprisingly, it was found that support-bound recombinant expression of heterologous polypeptides preferably in different compartments of a cell, e.g. of Gram-negative bacterial cells or of eukaryotic cells, leads to stable presentation of the heterologous polypeptides in a functional (i.e. immunologically or/and biologically, e.g. enzymatically, active) form. If the host cell is a Gram-negative bacterial cell, the cell compartments may preferably be selected from the cytosol, the cytoplasmic membrane (outside and inside), the periplasmic space and the outer membrane (outside and inside). If the host cell is a eukaryotic cell, said compartments may preferably be selected from the cytosol, the cytoplasmic membrane (outside and inside) and cell organelles such as, for example, Golgi, lysosomes, mitochondria, chloroplasts, vacuoles or endoplasmic reticulum.

The functional recombinant proteins present in the host cell are preferably cooperative, i.e. they fulfill a common immunological or/and biological function, for example as enzymes in a multistage reaction cascade.

At least one, preferably a plurality, of the functional recombinant polypeptides is bound to a support, for example in the form of fusion polypeptides, and contain at least one functional domain and at least one support domain. Preferred forms of support-bound polypeptides are S-layer structures (fusion polypeptides with S-layer support domains), membrane-bound polypeptides (fusion polypeptides with membrane-integrated support domains) or/and components of recombinant phage structures. If it is desired to export the functional polypeptides from the cytosol to other cell compartments, said polypeptides are expressed together with suitable targeting domains which facilitate export to the cell compartment desired in each case.

Examples of targeting domains are signalpeptide or/and helper sequences which facilitate passage through the membranes.

In a preferred embodiment of the invention, at least one of the support-bound polypeptides is present as recombinant S-layer structure. S-layers are crystalline bacterial cell surface proteins which are composed of identical self-assembled units. Genetic data and sequence information for various S-layer genes from microorganisms can be formed, for example, in Peyret et al. (Mol. Microbiol. 9 (1993), 97–109). These data are expressly incorporated by reference.

Preferred S-layer genes are the *B.stearothermophilus* PV72 genes sbsA and sbsB. The sequences of these genes can be found, for example, in the international patent application PCT/EP97/00432 which also discloses production of a recombinant S-layer fusion protein in the cytoplasm of Gram-negative host cells. The international patent application PCT/EP98/04723 in turn describes production of a recombinant S-layer protein in various compartments of Gram-negative bacteria cells or eukaryotic cells. Regarding the construction of recombinant S-layer genes and production of suitable expression constructs, these two said international applications are expressly referred to. However, no indication of coexpression of two different functional recombinant polypeptides is found there.

Surprisingly, it was found that it is possible to co-express simultaneously or/and sequentially a plurality of recombinant S-layer proteins, where appropriate in combination with further heterologous proteins, for example in various compartments of host cells, in particular of Gram-negative bacterial cells and eukaryotic cells.

The nucleotide sequence of the gene coding for the mature SbsA protein is indicated from position 91–3684 in SEQ ID No. 1. The corresponding amino acid sequence is depicted in SEQ ID No. 2. The nucleotide sequence of the gene coding for the mature SbsB protein is indicated from position 94–2763 in SEQ ID No. 3. The corresponding amino acid sequence is depicted in SEQ ID No. 4.

In a first preferred embodiment (sbsA), the nucleic acid coding for the support domain of a functional peptide is selected from (i) a nucleic acid which comprises the nucleotide sequence from position 91 to 3684 shown in SEQ ID No. 1, (ii) a nucleic acid which comprises a nucleotide sequence corresponding to the nucleic acid from (i) within the framework of the degeneracy of the genetic code, and (iii) a nucleic acid which comprises a nucleotide sequence hybridizing with the nucleic acids from (i) or/and (ii) under stringent conditions.

In a second preferred embodiment (sbsB), the nucleic. acid coding for the support domain of a functional peptide is selected from (i) a nucleic acid which comprises the nucleotide sequence from position 94 to 2763 shown in SEQ ID No. 3, (ii) a nucleic acid which comprises a nucleotide sequence corresponding to the nucleic acid from (i) within the framework of the degeneracy of the genetic code, and (iii) a nucleic acid which comprises a nucleotide sequence hybridizing with the nucleic acids from (i) or/and (ii) under stringent conditions.

"Stringent hybridization" in accordance with the present invention means that hybridization still occurs even after washing at 55° C., preferably 60° C., in an aqueous low-salt buffer (e.g. 0.2×SSC) (see also Sambrook et al. (1989), Molecular Cloning. A Laboratory Manual).

Preferred sites for inserting peptide- or polypeptide-coding sequences into the sbsA gene are regions between positions 200–3600 of the nucleotide sequence shown in SEQ ID No. 1. Particularly preferred insertion sites are the NruI cleavage site at position 585, the PvuII cleavage site at position 881, the SnaB I cleavage site at position 920, the PvuII cleavage site at position 2507 and the PvuII cleavage site at position 2652 (PCT/EP 97/00 432). Further preferred insertion sites are positions 562, 1087, 1813, 1947, 2295, 2652, 3046, 3484 and 3594. The positions indicated in each case refer to the first nucleotide of the insertion.

Preferred sites of insertion into the sbsB gene are regions between positions 200–2600 of the nucleotide sequence shown in SEQ ID No. 3. Particularly preferred insertion sites are positions 410 (codon 136), 484 (codon 161/162) and 1583 (codon 528/529) (PCT/EP 97/00432). Further preferred insertion sites are positions 598, 1012, 1435, 1808 and 2301, the position indicated in each case referring to the first nucleotide of the insertion.

Alternatively or additionally, it is also possible to produce support-bound polypeptides in a different form, for example as components of recombinant phage structures, e.g. ØX174 or ØCH1.

Yet another possibility of producing support-bound polypeptides is the synthesis as fusion polypeptides with membrane integration domains so that the functional polypeptides are located at the locations desired in each case (outside or inside of a membrane chosen in each case).

The support sequence used for integration into the outer membrane of prokaryotic Gram-negative host cells may be the C-terminal domain of IgA protease from Neisseria or Haemophilus (Klauser et al., J. Mol. Bio. 23.4 (1993), 579–593). Further suitable support domain sequences are OmpA or LamB sequences or parts thereof ( . . . ).

For integration into the cytoplasmic membrane of Gram-negative prokaryotic host cells, preference is given to using a hydrophobic nonlytical membrane-integrating protein domain which has an α-helical structure. Examples of DNA sequences coding for such a membrane-integrating protein domain are described in the European patent 0 516 655.

For secretion into the periplasm of Gram-negative prokaryotic cells it is possible to use, for example, the malE signal peptide sequence. Other sequences which cause secretion into the periplasm are described, for example, in Blondel and Bedouelle (Eur. J. Biochem 193 (1990), 325–330; Adip-Conquy et al. (Protein Eng. 8 (1995), 859–863); Weller et al (Eur. J. Biochem. 236 (1996), 34–39) and Dubreuil et al. (FEMS Immunol. Med. Microbiol. 13 (1996), 317–323).

Known signal peptides for expression in the cytoplasmic membrane or in organelles of eukaryotic cells are the N-terminal transit peptide of plastocyanin for transport into chloroplasts (Weisbeek et al., J. Cell. Sci. Suppl. 11 (1989), 199–223), mitochondrial signal peptides for transport into mitochondria (Skerjanc, Biochem. Cell. Biol. 68 (1990), 9–16), targeting sequences for transport into vacuoles (Vitale and Chrispeels, Bioessays 14 (1992), 151–160), targeting sequences for the cell membrane, cytoplasm and Golgi apparatus (Stanley, Mol. Membr. Biol. 13 (1996), 19–27), retention signals for the endoplasmic reticulum (Lencer et al., J. Cell. Biol. 131 (1995),:951–962) and transfer sequences for the Golgi apparatus or the plasma membrane (Rambourg et al., Anat. Rec. 245 (1996), 447–458).

It is possible for the DNA sequence coding for the foreign polypeptide to contain, in addition to the segment coding for the signal peptide, one or more further segments coding for further protein domains. Such a segment may preferably be located between the segment coding for the signal peptide and the segment coding for the foreign polypeptide. This segment preferably codes for a secretory polypeptide from Gram-negative bacterial or eukaryotic organisms or a part thereof. A preferred example of such a nucleic acid segment is the malE gene which encodes maltose binding protein.

The foreign polypeptides are preferably selected from DNA-binding epitopes, antigenic, allergenic or immunogenic epitopes, metal-binding epitopes, stretavidin, enzymes, cytokines or antibody-binding proteins.

A preferred example is stretavidin which is suitable for docking biotinylated reagents, e.g. after integration into the outer membrane. Another preferred example is antigenic, allergenic or immunogenic epitopes, for example epitopes from pathogenic microorganisms such as, for example, bacteria, fungi, parasites etc., and viruses, or epitopes from plants or epitopes against endogenous substances, e.g. cytokines, and also against toxins, in particular endotoxins. Particularly preferred examples of immunogenic epitopes are epitopes from viruses, for example from herpesviruses such as, e.g., herpesvirus 1, e.g. glykoprotein Δ, herpesvirus 6 or pseudorabies virus (Lomniczi et al., J. Virol. 49 (1984), 970–979), in particular epitopes from the gB, gC or/and gD genes, epitopes from foot-and-mouth disease virus (FMDV), in particular epitopes from the gene segments coding for VP1, VP2 or/and VP3, epitopes from flaviviruses or epitopes from filoviruses such as, for example, Ebola, Marburg or Lassa virus. The immunogenic epitopes may be selected such that they promote generation of an antibody-mediated immune reaction or/and promote generation of a cellular immune reaction, for example by stimulation of T cells. Examples of suitable allergenic epitopes are birch pollen allergens, e.g. Bet v I (Ebner et al., J. Immunol. 150 (1993) 1047–1054). Particular preference is furthermore given to antigenic epitopes which are capable of binding and filtering out endogenous or exogenous substances such as, for example, cytokines or toxins from serum or other body fluids. Epitopes of this kind may include components of cytokine or toxin receptors or of antibodies against cytokines or toxins.

Modified foreign polypeptides, for example S-layer proteins; which have immunogenic or/and antigenic epitopes with glycosylation sites, are preferably produced in eukaryotic host cells in which glycosylation is possible. In this connection it is also possible to glycosylate the natural S-layer sequences. Examples of potential N-glycosylation sites in the S-layer gene sbsA are amino acid positions 26, 285, 343, 384, 387, 388, 418, 421, 483, 653, 675, 902, 924, 1048, 1058, 1118, 1154 and 1161. A potential N-glycosylation in the sbsB gene can occur in positions 155, 184, 213, 302, 303, 400, 463, 606, 755 and 915. Further possible modifications of the sbsA gene include amidation, phosphorylation by casein kinase II, N-myristoylation and phosphorylation by protein kinase C. Further possible modifications of the sbsB gene include phosphorylation by CAMP and cGMP-dependent protein kinase, phosphorylation by casein kinase II, N-myristoylation, phosphorylation by protein kinase C and attachment to a fibronectin receptor (via sequence RGD).

Likewise preferred foreign polypeptides are cytokines such as, for example interleukines, interferons or tumor necrosis factors. These molecules may be used, for example, in combination with immunogenic epitopes for the production of vaccines. In addition, antibody-binding proteins such as, for example, protein A or protein G, or DNA- or/and metal-binding epitopes such as, for example, leucine zipper, zinc finger, etc are also preferred.

The recombinant polypeptides are particularly preferably enzymes, in particular enzymes which catalyze a multistage enzymatic reaction. Specific examples are enzymes for the synthesis of polyhydroxyalkanoates, e.g. polyhydroxybutyric acid synthase (Lubitz and Resch, DE 44 171 69 A1; Slater, S. C., Voige W. H., Dennis, A. E. J. Bacteriol. (1998), 170:4431).

The present invention still further relates to recombinant bacterial ghosts obtainable from a Gram-negative host cell of the invention, which has at least two functional recombinant polypeptides bound to a support.

The preparation of suitable "bacterial ghosts" is described, for example, in the international patent application PCT/EP91/00967 which is hereby incorporated by reference. Said patent application discloses modified bacteria obtainable by transformation of a Gram-negative bacterium with the gene of a lytic membrane protein from bacteriophages, with the gene of a lytic toxin-releasing protein or with genes which contain part sequences thereof coding for lytic proteins, culturing of the bacterium, expression of this lysis gene and isolation of the resulting bacterial ghost from the culture medium.

As described in the European patent 0 516 655, the membrane of these bacteria may have bound to it a recombinant protein which is obtainable by expression of a recombinant DNA in these Gram-negative bacteria. This recombinant DNA comprises a first DNA sequence which codes for a hydrophobic, nonlytic membrane-integrating protein domain which has an α-helical structure and consists of 14–20 amino acids which may be flanked N- and C-terminally by in each case 2–30 amino acids of any kind. This first DNA sequence is operatively linked to a second DNA sequence which codes for a desired recombinant protein. Furthermore, the Gram-negative bacterium contains a third DNA sequence which is controlled separately from the first and second DNA sequences and codes for a lytic membrane protein from bacteriophages or a lytic toxin-releasing protein or for lytic parts thereof. Expression and lysis of recombinant Gram-negative bacteria of this type produce so-called "bacterial ghosts" which contain an intact surface structure with immunogenic epitopes bound to the surface.

The preparation of host cells of the invention is preferably carried out by a method in which
  (a) a host cell which has been transformed with at least two nucleic acids coding for recombinant polypeptides is provided, at least one of the nucleic acids being linked to a sequence coding for a support domain, in order to facilitate expression of the recombinant polypeptide in a support-bound form,
  (b) the host cell is cultured under conditions which lead to expression of the nucleic acids and to a generation of the polypeptides encoded thereby in a functional form.

Furthermore, the nucleic acids coding for the recombinant polypeptides are preferably operatively linked to sequences which provide for localization of the recombinant polypeptides in each case in different compartments of the host cell.

When expressing the recombinant proteins in support-bound form as modified S-layers, it is in addition also possible to express genes in the cell which code for an unmodified S-layer protein. In this case, it is possible for the modified S-layer proteins to form an S-layer structure which is compatible with the unmodified S-layer proteins. An example of this embodiment of the method of the invention is an *E.coli* cell transformed with four S-layer genes, two of which are natural sbsA or sbsB genes and the other two are recombinant sbsA or sbsB genes.

The nucleic acids coding for the recombinant polypeptides are preferably located on recombinant vectors which contain at least one copy of the nucleic acid. The vectors used may be conventional prokaryotic or eukaryotic chromosomal or extrachromosomal vectors. Examples of such vectors are described in Sambrook et al., supra. The vectors contain the nucleic acids coding for the recombinant polypeptides, operatively linked to an expression control sequence active in the particular host cell. The expression control sequence particularly preferably comprises a controllable promoter. Examples of suitable prokaryotic promoters are the tac, lac, trp and λ promoters. Examples of suitable eukaryotic promoters are the SV40, CMV and metallothionein promoters. The at least two nucleic acids coding for heterologous polypeptides are particularly preferably expressed by using two different controllable promoters, for example two different temperature-sensitive λ promoters, as already described.

The recombinant host cells (living host cells or ghosts) are suitable for a multiplicity of applications. A use as vaccine or adjuvant is preferred, and in this case recombinant polypeptides are used which comprise immunogenic epitopes of pathogenic and/or endogenous immunostimulating polypeptides such as, for example, cytokines.

Particular preference is given to using the host cells or/and bacterial ghosts of the invention as enzyme reactors.

The present invention is furthermore illustrated by the following examples and figures, in which SEQ ID NO. 1 shows the complete nucleotide sequence of the coding segment of the B.stearothermophilus S-layer gene sbsA;
  SEQ ID NO. 2 shows the amino acid sequence derived therefrom;
  SEQ ID NO. 3 shows the complete nucleotide sequence of the coding segment of the B.stearothermophilus S-layer gene sbsB;
  SEQ ID NO. 4 shows the amino acid sequence derived therefrom.

FIG. 1 shows a diagrammatic representation of the possibilities for locating heterologous polypeptides in different compartments of a Gram-negative bacterial cell.
  (a) A Gram-negative bacterial cell is composed of the cytoplasm (cy), the inner membrane (im), the periplasm (pp) and the outer membrane (om).
  (b) Heterologous polypeptides can be exported to the periplasm by linkage with suitable targeting sequences (pe).
  (c) Heterologous polypeptides can be anchored on the inside of the inner membrane (mae).
  (d) In the periplasm, heterologous polypeptides can be immobilized in the form of recombinant S-layers (sie).
  (e) Not only one but a plurality of species of recombinant heterologous polypeptides can be immobilized as S-layers in the periplasm.

FIG. 2 shows the diagrammatic representation of a recombinant bacterial cell of the invention, which contains various heterologous polypeptides (e.g. enzymes) in different compartments.

EXAMPLES

1. Bacteria Strains, Media and Plasmids

Gram-positive bacteria of Bacillus stearothermophilus PV72 strain were cultured at 58° C. in SVIII medium (Bartelmus and Perschak, Z.Zuckerind.7 (1957), 276–281). E.coli bacteria were cultured in LB medium (Sambrook et al., (1989), supra). For the selection of transformants, ampicillin was added to the medium at a final concentration of 100 μg/ml. The plasmid pPlcAT10 (λpL, bla, colE1) (Stanssens et al., Gene 36 (1985), 211–223) was used as cloning vector.

2. Manipulation of DNA Fragments

DNA restriction analysis, agarose gel electrophoresis and cloning of DNA fragments were carried out according to the standard methods described in Sambrook et al. (1989), supra.

Competent cells were transformed by electroporation using a Bio-Rad Gene Pulser (Bio-Rad Laboratories, Richmond, Calif., USA) following protocols of the manufacturer.

Plasmid DNA was isolated according to the method of Birnboim and Doly (Nucleic Acids Res.7 (1979), 1513–1523). Chromosomal DNA was isolated according to the methods described in Ausubel et al. (Current Protocols in Molecular Biology (1987), New York, John Wiley).

Restriction endonucleases and other enzymes were obtained from Boehringer Mannheim, New England Biolabs or Stratagene and used according to the manufacturers' instructions.

3. DNA Sequencing

Sequence analysis of DNA molecules was carried out according to the dideoxy chain termination method of Sanger et al. The primers used for sequencing the sbsA gene were constructed on the basis of the already published sbsA sequence (Kuen et al., Gene 145 (1994), 115–120).

4. PCR Amplification of sbsA

PCR amplification of the sbsA gene was carried out according to example 4 of PCT/EP98/04723.

The PCR-amplified products were electrophoretically fractionated on a 0.8% agarose gel and purified for cloning using the Gene Clean system (BIO101 La Jolla, Calif., USA).

5. Cloning of the SbsA Gene 5.1 Cytoplasmic Expression Vector

The sbsA gene, obtained by PCR and 3.79 kb in length, was purified and cleaved with restriction endonucleases XbaI and BamHI. The resulting XbaI-BamHI fragment was cloned into the corresponding restriction sites of vector pPLcAT10 so that the sbsA gene was under transcriptional control of the pL promoter located upstream. The ATG start codon of the sbsA sequence was reconstructed by the cloning procedure. The cloned sbsA sequence contained the N-terminal sbsA signal sequence and ended 20 nt after the transcription terminator. The resulting vector was denoted pBK4.

5.2 Periplasmic Expression Vector

The sbsA gene was cloned without signal sequence and with a stop codon at the 3' end into the polylinker of the commercially available plasmid pMAL-P2 (New England Biolabs). The resulting pMAL-A plasmid contains a tac promoter-controlled fusion gene comprising the malE gene including the signal sequence thereof and also the sbsA gene without the signal sequence thereof. A factor Xa cleavage site is located between the two domains.

6. Recombinant Coexpression of the SbsA Gene in the cytoplasm and Periplasm of E.coli E.coli K12 cells, cotransformed with pBK4 and pMAL-A, were cultured at 28° C. until reaching an optical density $OD_{600}$ of 0.3. Then cytoplasmic expression of sbsA was induced by increasing the culturing temperature from 28° C. to 42° C. Periplasmic expression of sbsA was induced by adding 1 mM of the lac inducer IPTG. 1.5 ml aliquots were removed before and 1, 2, 3 and 5 hours after induction of sbsA expression. E.coli pop2135/pPLcAT10 (cultured under the same conditions) and B.stearothermophilus PV72 were used as controls.

Culture supernatants and cell extracts from all samples were studied for expression of the S-layer protein by SDS-PAGE and Western immunoblotting.

For the Western blot, the proteins were transferred onto a nitrocellulose membrane and incubated with a polyclonal anti-SbsA antiserum from rabbits. Preparation of this antiserum is described in Egelseer et al. (J Bacteriol.177 (1995), 1444–1451). Bound SbsA-specific antibodies were detected using a conjugate of goat anti-rabbit IgG and alkaline phosphatase.

In cytoplasmic extracts of the cotransformed E.coli cells an additional strong protein band having about the same molecular weight as the wild type SbsA protein was found.

Analysis of the crude extract of E.coli DH5α cells (Hanahan (1983) supra) transformed with PMAL-A showed expression of a MalE-SbsA fusion polypeptide having a molecular weight of approx. 170 kDa in the periplasmic fraction of the cell extract, which was produced by a cold osmotic shock.procedure (Neu and Heppel, J. Biol. Chem. 240 (1965); 3685–3692).

7. Coexpression of the SbsB )Protein in the Cytoplasm and Periplasm

As described in examples 5 and 6, the sbsB gene was cloned into plasmids pMAL-P2 and pPLcAT10, resulting in plasmids pMAL-B and pBK6.

It was possible to detect the presence of the SbsB protein in the cytoplasm and periplasm of E.coli cells transformed with plasmids pMAL-B and pBK6.

8. Immobilized PHB Synthase in the Cytoplasmic Membrane of E.coli

Polyhydroxyalkanoates (PHA) are bacterial storage substances which are formed in a natural producer when phosphorus, sulfur or oxygen are limited but a carbon source is sufficiently present. They consist of esterified monomers of hydroxy fatty acids and form water-insoluble polymers which are distinguished depending on the position of the hydroxyl group and the length of the side chains. The most prominent PHA is poly(R)-3-hydroxybutyrate (P(3-HB)), an unbranched homopolymer of (R)-3-hydroxybutyric acid P(3-HB)).

In the Gram-negative, facultative chemolithotrophic oxyhydrogen bacterium Ralstonia eutropha the genes responsible for PHB systhesis, phbA, phbB and phbc, are organized in one operon (phbCAB) (Schubert et al., J. Bacteriol (1998), 170:5837). The nucleotide sequences of the open reading frames and also of the translation regions of said genes have been published (Steinbuchel, A. Polyhydroxy alcanoic acids, in: Biomaterials (1991), 123–213).

Within the study of the structure/function relation of PHB synthase, various insertion mutants and deletion mutants and also fusion proteins were prepared and changes in the enzyme activity were determined (Kalousek, S. PhD thesis, University of Vienna (1993)). From this work, plasmid pPHB-L originates which contains a gene which codes for a fusion protein composed of P(3-HB) synthase (588 of 590 amino acids) and a membrane anchor from the C-terminal sequence of the lysis protein of phage MS2. Cells growing on solid medium+1% glucose accumulate up to 60% (w/w) P-(3-HB) granules when expressing pPHB-L.

The membrane-anchored PHB synthase thus is enzymatically fully functional.

9. Recombinant Expression of (2,5-diketo-D-gluconic Acid) Reductase From a Plasmid in Bacteria; and Immobilization Thereof to Bacterial S-layers Expression of a recombinant plasmid in a bacterial strain should enable said strain to produce 2-KLG directly from D-glucose in a single step (single fermentation). For this purpose, an enzyme required for the reduction to 2-KLG (2,5-DKG reductase from Corynebacterium sp. ATTC. 31090) was cloned into a strain producing 2,5-diketo-D-gluconic acid (2,5-DKG).

Using the vector pSL coding for a surface layer gene (sbsA) increased the stability of 2,5-DKG reductase. In this connection the S-layer protein (SbsA)-served as a matrix for 2,5-DKG reductase. By inserting 2,5-DKG reductase at 4 different sites within the sbsA gene, a recombinant protein having the ability to form self-assembly products was found.

To this end, sbsA-2,5 dkg reductase fusion genes were prepared which-carry the 2,5-dkg gene at.four different positions of the sbsA gene (positions 581, 881, 916 and 2649). *E.coli* pop2135 served as host cell. Correct cloning was checked by sequence analyses of the inserted gene and the neighboring regions. It was possible by SDS-PAGE and Western blot analyses to show stable expression of the fusion proteins. After successful expression in *E.coli*, the plasmids were transformed into Pectobacterium cypripedii HaPO1.

It was possible by means of SDS-PAGE and Western blot to detect in P.cypripedii HaPO1, too, stable expression of the SbsA-2,5 DKG reductase fusion protein.

10. Other Enzymes Immobilized to S-layers

The enzyme luciferase (genes luxA and luxB) and green fluorescent protein (gfp) were also fused to the sbsA gene, in order to generate in this way light and fluorescence, respectively.

---

What is claimed is:

1. A host cell comprising at least two functional heterologous recombinant polypeptides, at least one of which is present as an s-layer structure in a support-bound form, and the polypeptides being located in each case in different compartments of the host cell.

2. The cell according to claim 1, wherein the cell is a gram-negative bacterial cell.

3. The cell according to claim 1, wherein the compartments are selected from the group consisting of cytosol, the outside and inside of the cytoplasmic membrane, the periplasmic space and the outside and inside of the outer membrane.

4. The cell according to claim 1, wherein the cell is a eukaryotic cell.

5. The cell according to claim 1, wherein the compartments are selected from the group consisting of cytosol, the outside and inside of the cytoplasmic membrane and cell organelles.

6. The cell according to claim 1, wherein a plurality of the recombinant polypeptides are bound to a support.

7. The cell according to claim 1, wherein the polypeptides in a support-bound form are present in the form of fusion polypeptides having support domains.

8. The cell according to claim 1, wherein the polypeptides in a support-bound form are present in the form of S-layer structures, membrane-bound polypeptides and/or as components of recombinant phage structures.

9. The cell according to claim 1, wherein the recombinant polypeptides are selected from the group consisting of enzymes, cytokines, antibody-binding proteins, DNA-binding epitopes, antigenic, allergenic and immunogenic epitopes and streptavidin.

10. The cell according to claim 1 or 9, wherein the recombinant polypeptides are enzymes.

11. The cell according to claim 10, wherein the enzymes catalyze a multistage enzymatic reaction.

12. The cell according to claim 11, wherein the enzymes catalyze the synthesis of polyhydroxy-alkanoates.

13. A recombinant bacterial ghost obtainable from a gram-negative cell according to claim 1, comprising at least two functional recombinant polypeptides bound to a support.

14. A method for preparing a host cell according to claim 1, comprising the steps of (a) providing a host cell which has been transformed with at least two nucleic acids encoding polypeptides, at least one of which is linked to a sequence encoding a support domain in order to facilitate expression of the polypeptide in a support-bound form, and (b) culturing the host cell under conditions which induce expression of the polypeptides by the nucleic acids encoding the polypeptides.

15. A vaccine comprising a host cell of claim 1 or a ghost of claim 13.

16. An enzyme reactor comprising a host cell of claim 1 or a ghost of claim 13.

* * * * *